United States Patent [19]

Rol

[11] Patent Number: 4,664,490

[45] Date of Patent: May 12, 1987

[54] CONTACT LENS FOR OPHTHALMOSCOPY AND OPHTHALMOTHERAPY BY MEANS OF LASER BEAM

[75] Inventor: Pascal Rol, Gunten, Switzerland

[73] Assignee: Lasag AG, Thun, Switzerland

[21] Appl. No.: 729,716

[22] Filed: May 2, 1985

[30] Foreign Application Priority Data

May 17, 1984 [FR] France ............... 84 07835

[51] Int. Cl.$^4$ ............... A61B 3/00; G02C 7/04; G02C 7/02
[52] U.S. Cl. ............... 351/219; 351/160 R; 351/176
[58] Field of Search ............... 351/219, 160 R, 176

[56] References Cited

U.S. PATENT DOCUMENTS

| | | | |
|---|---|---|---|
| 4,067,646 | 1/1978 | Nohda ............... | 351/219 |
| 4,439,026 | 3/1984 | Wilms ............... | 351/219 |
| 4,506,962 | 3/1985 | Roussel ............... | 351/219 X |
| 4,568,157 | 2/1986 | Kurwa ............... | 351/219 X |
| 4,598,984 | 7/1986 | Rol . | |

FOREIGN PATENT DOCUMENTS 59159 9/1982 European Pat. Off. .

Primary Examiner—Rodney B. Bovernick
Attorney, Agent, or Firm—Pollock, Vande Sande & Priddy

[57] ABSTRACT

The invention concerns a contact lens for observation or treatment by irradiation of the eye, in particular the anterior chamber, outside of the optical axis of the eye. The contact lens comprises a Goldmann or Roussel lens having an entrance face which is flat or spherical, a spherical exit face which is applied to the cornea of the eye, a reflecting face and a compensating element, for example a plano-cylindrical lens. The compensating element is fixed on the reflecting face and its function is to create an astigmatism effect which is the reverse of that of the eye, for an incident light beam which enters by way of the entrance face. The contact lens permits highly accurate focusing of the beam on the apex inside the eye, which is particularly useful in ophthalmoscopy and ophthalmotherapy by means of a laser beam.

7 Claims, 4 Drawing Figures

CONTACT LENS FOR OPHTHALMOSCOPY AND OPHTHALMOTHERAPY BY MEANS OF LASER BEAM

The present invention concerns a contact lens for observation of the interior of the eye and treatment thereof by irradiation, primarily at the location of the anterior chamber.

The eye may be the seat of various diseases and disorders which affect inter alia the iris, the crystalline lens or the apex of the anterior chamber. In order to diagnose the disorder, the interior of the eye must be optically inspected in a precise fashion.

Various methods of observation are known. The best images are obtained when the method involves using a contact lens which is fitted to the eye, permitting minimum deformation of the beam of light which issues from the point observed, or working point, which is inside the eye. Goldmann and Roussel contact lenses may be mentioned by way of example. The former is described in particular in the publication entitled "Gonioscopie und Goniofotographie" by Winfried Muller and Hans-Peter Brandt, Ferdinand Enke edition, Stuttgart 1979, while the latter is described in published European patent application No. 59159.

The Goldmann lens presents to the incident light beam a flat entrance face and a spherical exit face which is intended to be applied to the cornea. It may also comprise one or more flat reflecting faces or surfaces forming mirrors in order to permit indirect observation of the interior of the eye. The Roussel lens in turn has a curved entrance face forming a phase surface for the incident beam, and an exit face which is also spherical.

Ophthalmological doctors are highly appreciative of those two contact lenses for observation purposes, having regard to their handleability and the degree of comfort in use that they provide. However, the quality of the image that they produce suffers from deterioration for light beams which are remote from the optical axis of the eye.

If a contact lens can be used for observing the interior of the eye, it becomes indispensable for irradiation treatment of the anterior chamber. However, when operating under conditions which are different from the conditions involved in observation, it must comply with requirements of greater severity.

In fact, treatment of the interior of the eye by irradiation is effected by focusing an intense beam of coherent light on the diseased or disordered region or a part of that region. The beam of light can be produced for example by a Nd-YAG or Argon laser.

In order to make the treatment effective and without danger, it is necessary for the beam reaching the working point to be very well focused and highly convergent or open, that is to say, the angle formed by the extreme rays of light must be large. The condition in regard to good focusing is obvious as it permits the working point to be located with a high degree of accuracy and enables a substantial amount of energy to be concentrated at that location. The condition of substantial convergence reinforces the condition just discussed. In fact, it permits the working point to be satisfactorily located in respect of depth. On the other hand, the energy density of the light beam then falls away rapidly outside the working point, which has the consequence of reducing the danger of lesion of the healthy parts of the eye. The degree of focusing of the light beam will be improved in proportion to decreasing values in respect of spherical aberration and astigmatism defects of the optical system through which the light beam passes, formed by the contact lens and the eye. Now, such defects generally increase with the diameter or convergence of the incident beam. Those two conditions are therefore contradictory and it is necessary to find a compromise for each particular situation of use. The Goldmann lens does not satisfactorily solve the problem involved in the convergence of the light beam and is even less satisfactory in regard to the problem regarding astigmatism.

Various improvements have been made in the Goldmann lens. Thus, versions of that lens which have higher levels of performance are known, for example the Roussel lens, which has already been referred to above, having been developed more recently. The non-flat entrance face of that lens does in fact make it possible to reduce the aberration phenomena and to increase the degree of opening of the beam.

It should also be noted that all the attempts to improve the Goldmann lens were made by considering the contact lens in itself, without having regard to the optical properties of the eye which was to be observed or irradiated. Thus, a contact lens which does not give any defect would not permit perfect focusing of a light beam at a point in the anterior chamber which is spaced from the axis of the eye. In fact, to reach that point, the beam must pass through different parts of the eye and in particular the cornea which gives an astigmatism defect which increases in magnitude in proportion to the increase in the angle of incidence at which it is viewed. That has the effect of causing a deterioration in the light beam. Now, no contact lens, whether of the Goldmann type or otherwise, takes account of that phenomenon, which is a highly inconvenient defect in known lenses which are intended for treatment of the anterior chamber at points which are away from the axis of the eye.

The main object of the present invention is to provide a contact lens which is intended for examination and treatment by irradiation of the different internal parts of the eye, primarily the anterior chamber, which does not suffer from the above-indicated disadvantages.

SUMMARY OF THE INVENTION

To attain that object, the contact lens according to the invention for observation and treatment of the eye by means of a light beam is of the type comprising a principal element provided with an entrance face by way of which the beam enters, an exit face which is intended to be applied to the cornea of the eye and by way of which the beam issues towards a working point within the eye, and a reflecting face whose function, by total reflection, is to divert the beam entering the entrance face towards the exit face. The contact lens is distinguished by a compensating element which is associated with the reflecting face, the function of which is to create in the contact lens an astigmatism defect which is the reverse of that of the eye.

An advantage of the contact lens according to the invention is to permit precise focusing of an incident light beam at a point in the anterior chamber, in spite of the optical defects in the parts of the eye through which the light beam passes.

BRIEF DESCRIPTION OF THE DRAWINGS

Other advantages will be apparent from the description which will be set out below with reference to the accompanying drawing which illustrates a contact lens according to the invention, solely by way of non-limiting example. In the drawing in which the same elements are denoted by the same references.

DESCRIPTION OF PREFERRED EMBODIMENTS

Figure 1:
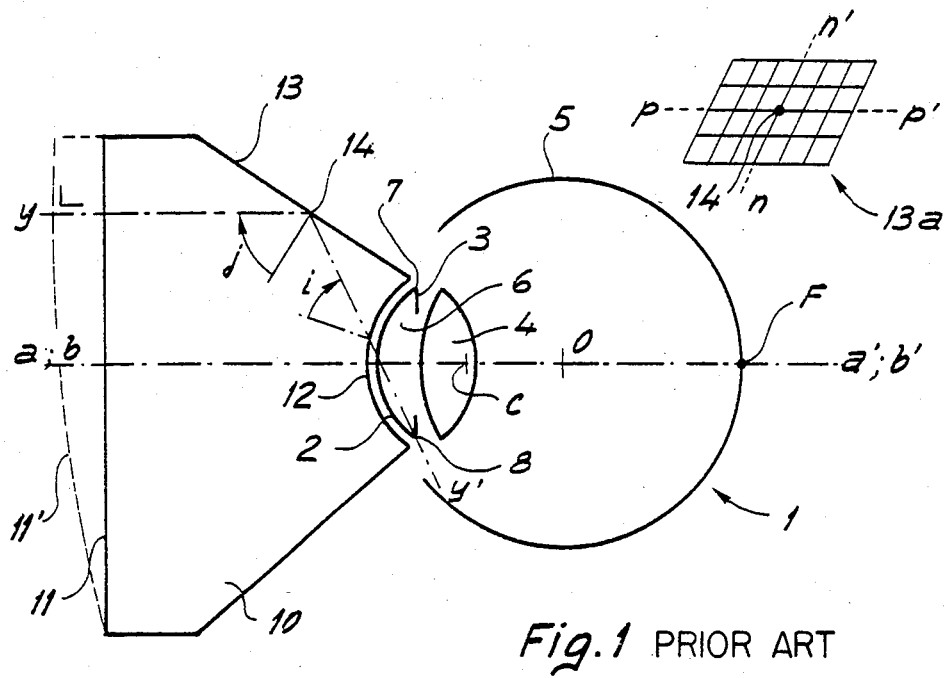
FIG. 1 is a diagrammatic view in section taken along a longitudinal plane of symmetry of the eye, with a Goldmann contact lens as referred to above applied to the cornea thereof.

A diagrammatic view of the eye is shown in FIG. 1, in longitudinal section along a plane of symmetry. It is a body of revolution having an axis of symmetry aa' which comprises, moving from the outside inwardly of the eye, a spherical cornea 2 having point C as its centre of curvature and by way of which the light rays enter the eye, an iris 3 whose aperture controls the amount of light, a crystalline lens 4 and a retina 5 of spherical shape having a centre O, through which the axis aa' passes at a point F. The cornea 2 and the crystalline lens 4 define a volume which is identified by reference numeral 6 and which is called the anterior chamber. The location at which the cornea 2 and the iris 3 meet defines a circle 7, each point theron, such as for example the point denoted by reference numeral 8, being referred to as an apex.

In order properly to understand the present invention, it will be appropriate firstly to describe the structure of the mirror-type Goldmann contact lens which is already known in the art and which is also shown in cross-section in FIG. 1. This lens of generally conical shape, as indicated by reference numeeral 10, comprises a flat entrance face 11 forming the base of the cone, a spherical exit face 12 having a centre of curvature C close to the top of the cone, and a flat mirror or reflecting face 13 which is machined on the side face of the cone. The exit face 12 is applied to the cornea 2. The light rays undergo total reflection at the reflecting face. A part of that mirror is shown as a diagrammatic perspective view at 13a, wherein the axis pp' is a straight line in the plane of FIG. 1 and the axis nn' is a straight line which is perpendiculr to that plane. Other reflecting faces (not shown) may be distributed around the periphery of the lens. The angle between a reflecting face and the entrance face depends on the point aimed at and it may vary between 50° and 80°. The line perpendicular to the entrance face 11, which passes through the centre of curvature C of the exit face 12, defines the axis of symmetry bb' of the contact lens 10. In the construction shown in FIG. 1, the axis aa' and bb' are coincident. The dimensions of the lens 10 permit it to be moved pivotally over the cornea 2 so that the point of observation or treatment, which is also referred to as the working point, in the interior of the eye, may be displaced within certain limits. The axis bb' then pivots about the centre of curvature C which is common to the cornea 2 and to the exit face 12.

The Roussel lens is of general cylindrical shape, while its section is almost identical to that of the Goldmann lens shown in FIG. 1. Thus, it comprises an exit face 12 and a reflecting face 13. In contrast, its entrance face is in the form of a portion of a sphere, as indicated at 11', instead of being flat. The centre of curvature (not shown) of the portion of the sphere is disposed on the side of the exit face 12 and is moved out of centre towards the reflecting face 13 with respect to the axis bb'.

The field of use of the Goldmann lens is fairly wide since virtually all the essential points of the interior of the eye are accessible thereto, both for the purposes of observation and for treatment.

The aim of the present invention being to provide a modified Goldmann or Roussel lens which makes it possible to observe and in particular to effect irradiation treatment on any point of the anterior chamber 6 under good conditions, FIG. 1 shows the path followed by the light in a Goldmann lens when aiming at the apex point 8. To attain the point 8, a light beam Y of which only the axis yy' is shown, after entering the lens 10 perpendicularly to the face 11 or to the face 11' in the case of the Roussel lens, must undergo total reflection by the face 13 at a point 14 in order to pass into the eye 1 at an angle of incidence i which is measured with respect to the line normal to the exit face 12 at that point. The total reflection means that the face 13 does not need to be covered by an opaque reflective layer.

As the eye is not a perfect optical system, even a contact lens which does not give rise to any defect will not permit a light beam to be focused at a point, but only at best to a circle of diffusion of more or less small diameter. In fact, the eye has an astigmatism defect which become more pronounced in proportion to an increase in the angle of incidence i of the light beam passing through the cornea. In order to achieve more precise focusing, the contact lens must therefore have an astigmatism defect which is the opposite to that of the eye.

There are a number of models of the eye, for example the Gullstrand-Legrand model or the Littmann model, which permit the optical properties of the eye to be described with a high degree of accuracy. It is also well known that the surface of the eye, like any spherical optical surface, when an incident beam passes therethrough, gives rise to an astigmatism defect which may be broken down into a sagittal part and a tangential part. Each part is defined by its focal length, measured for example from the entrance face of the eye. The focal length corresponding to the sagittal part is denoted by S while that corresponding to the tangential part is denoted by T.

Theoretical considerations and tests have shown that it is possible to produce a compensated contact lens having the required opposite astigmatism defect by associating with the reflecting face 13 of a Goldmann lens a compensating element which is of a simple form and which is easy and inexpensive to produce.

The compensating element can modify the point of sight of the Goldmann lens. However, that modification remains of small magnitude and it can be compensated by a slight change, a few degrees at maximum, in the inclination of the reflecting face. In practice, for each point of sight, it is always possible to produce or find a suitable lens of the Goldman type. In fact, there exist standard lenses in which the inclination of the reflecting face, with respect to the entrance face, is between 50° and 80°.

Figure 2A:
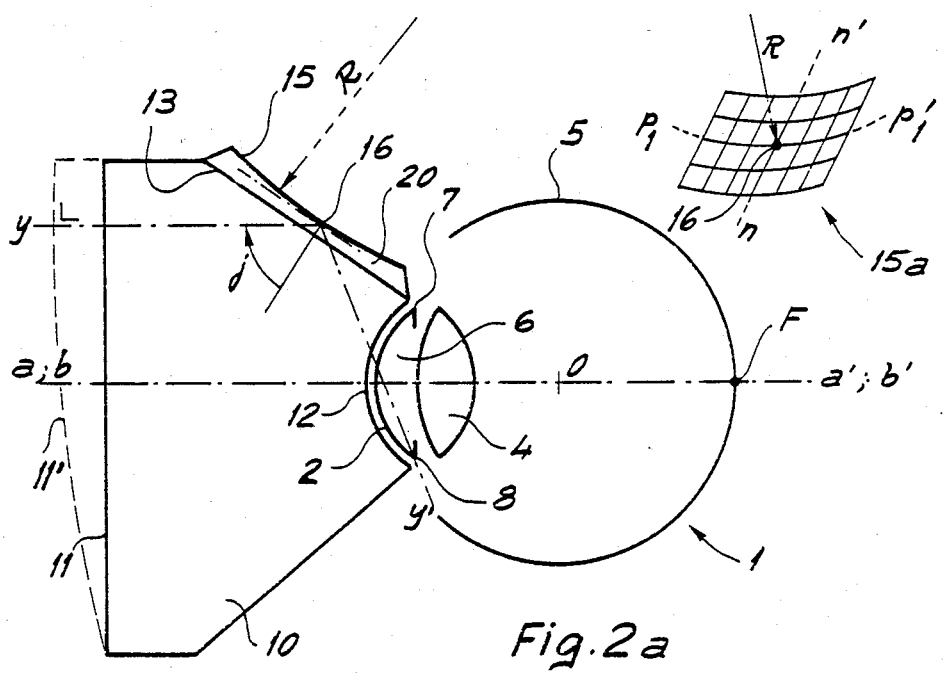
FIGS. 2a to 2c show embodiments of the contact lens according to the invention.

A first embodiment of a compensated contact lens according to the invention is shown in longitudinal section along a plane of symmetry of the lens, in FIG. 2a. In that embodiment, the compensating element is a plano-cylindrical lens 20 whose axis is perpendicular to the plane of the drawing. The lens 20 which has a flat face and a cylindrical face 15 is so oriented that the flat face thereof is applied against the reflecting face 13 of the Goldmann lens 10. The cylindrical face 15 of the lens 20 has a radius of curvature R, the centre of curvature being disposed on the same side as the face 15 with respect to the face 13. A part of the face 15 is shown in perspective at 15a wherein pp' represents a circular arc which is disposed in the plane of FIG. 2a and nn' represents a straight line which is perpendicular to that plane.

FIG. 2a also shows the path of a light beam having an axis yy' which terminates at the apex point 8 in the situation where the Goldmann lens 10 and the prism 20 are made to the same material. The beam of light which passes into the Goldmann lens 10 perpendicularly to the face 11 passes through the face 13 without undergoing any deflection, the materials on respective sides of that face being identical, to reach the cylindrical face 15 of the lens 20 at a point 16 at an angle of incidence j. After having experienced total reflection at the point 16, the beam leaves the face 15 at the same angle j to pass into the anterior chamber 6 which it passes through until reaching the apex point 8.

It will be appreciated that, as the face 15 is cylindrical, the angle j varies with the position of the point 16 which depends on the point of impingement of the beam yy' on the face 11. However, as the radius of curvature R is in practice very large with respect to the dimensions of the lens 20, the limited movements that the beam yy' may experience only give rise to very small variations in the angle j, which will be considered as being constant.

In the embodiment of the compensated contact lens shown in FIG. 2a, the compensating element is the plano-cylindrical lens 20. Now, it is well known that such a lens has an astigmatism defect, in regard to the light beam having the axis yy'. Such astigmatism depends on the angle j, the distance e (not shown in the drawing) which is covered by the beam yy' between the face 15 and the face 12, and the radius of curvature R of the face 15.

If $R=2(T+e)(S+e)/[(T-S) \cos j]$, S and T, as already mentioned, being the focal lengths respectively corresponding to the sagittal and tangential parts of the astigmatism, then the astigmatism of the lens 20 becomes precisely the reverse to that of the eye, thus producing the required correction in the Goldmann lens. Typically, R is about 3.50 m.

It will be appreciated that the corrected contact lens shown in FIG. 2a may be made in one piece. On the other hand, it is apparent that only the part of the lens 20 which receives the light beam having the axis yy' is functional. The remainder of the lens may be of any form.

Figure 2B:
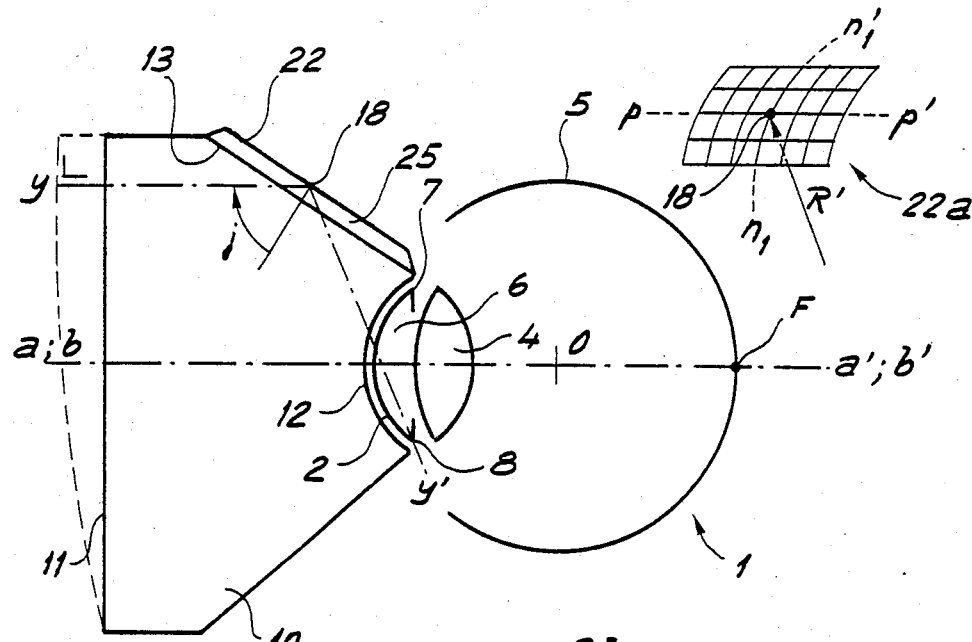

A second embodiment which uses a plano-cylindrical lens 25 as the compensating element is shown in FIG. 2b. That lens 25 has a flat face and a cylindrical reflecting face 22. It is positioned in such a way that its flat face is applied to the face 13 of the Goldmann lens 10 and the axis of the face 22 is disposed in the plane of the drawing. The face 22 has a radius of curvature indicated by R', with the centre of curvature being disposed on the same side as the face 13. A part of the cylindrical face 22 is shown in perspective at 22a wherein pp' is a straight line disposed in the plane of FIG. 2b and $n_1n_1'$ is a circular arc which is disposed in a plane perpendicular to the above-mentioned plane. Finally, the path of a light beam having an axis yy' is also shown in FIG. 2b, assuming, as in the previous case, tha the Goldmann lens 10 and the lens 25 are made of the same material.

The beam of light meets the face 22 at a point 18 at an angle of incidence j, where total reflection deflects it towards the apex point 8, while making it cover the distance e between the faces 22 and 12.

In order for the lens 25 to have an astigmatism defect which is precisely the reverse to that of the eye, the radius of curvature R' of the reflecting face 22 must be of a clearly defined value which is given by the relationship: $R'=[2(T+e)(S+e) \cos j]/(S-T)$. Typically, R' is 0.974 m.

The relationships giving R and R' are based on the optics formulae which are known by the name of the Coddington equation, appearing for example on pages 186 and 187 of the work "Lens Design Fundamentals" by Rudolph Kingslake, Academic Press, New York, 1978.

Figure 2C:
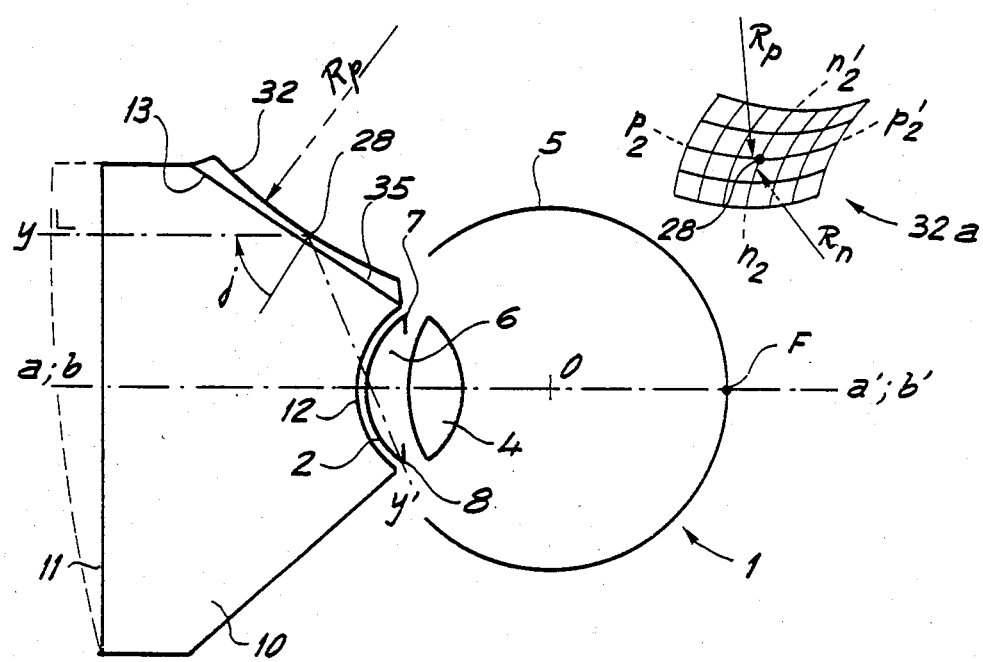

A third embodiment is shown in FIG. 2c. In this case, the compensating element is a plano-toric lens 35. The lens 35 has a flat face and a toric reflecting face 32. The face 32 is defined by two principal radii of curvature Rp and Rn giving circles in two perpendicular planes from two difference centres of curvature. The first centre of curvature which corresponds to the radius Rp is disposed on the same side as the face 32 with respect to the flat face of the lens 35 and the second centre of curvature which corresponds to the radius Rn is disposed on the side opposite to the face 32, with respect to the same flat face. The lens 35 is positioned and oriented on the Goldmann lens 10 in such a way that the flat face of the lens 35 comes into contact with the face 13 and the plane of the circle described by the radius Rp coincides with the plane of the drawing. A part of the face 32 is shown at 32a in which $p_2p_2'$ represents a circular arc of a radius Rp which is disposed in the plane of FIG. 2c and $n_2n_2'$ represents a circular arc having a radius Rn which is disposed in a plane perpendicular to the plane of FIG. 2c.

Assuming, as in the previous cases, that the Goldmann lens 10 and the lens 35 in FIG. 2c are made of the same material, a light ray having the axis yy' will reach the face 32 at a point 28 in order there to undergo total reflection, directing it towards the apex point 8.

It is known that a toric surface gives rise to an astigmatism defect which depends on the radii Rp and Rn. The Coddington equations already referred to above make it possible to determine such radii so that the astigmatism of the lens 35 precisely compensates for the astigmatism of the eye. A number of solutions are possible, for example Rp=7.0 m and Rn=1.93 m.

The compensating element and the Goldmann lens may be made of the same material, in the form of two separate components. Once those two components are joined together, they provide for physically defining the face 13 in the contact lens which is produced in that way. However, that face has no effect on the light beams, as the refractive indices of the two sides of the face are the same. Therefore, the compensated contact lens may equally well be made in one homogenous piece in which the face 13 can no longer be specifically located. It will be appreciated that the resulting one-piece lens will have the same properties as the lens referred to above. Materials with different refractive indices may obviously also be used for the compensating element and the Goldmann lens. In that case, the rays of the light beam having the axis yy' will experience a first refraction effect at the location of the face 13, on passing into the compensating lens and, after having been reflected, they will undergo a second refraction effect at the same face, on passing into the Goldmann lens. It will be appreciated that the calculation in respect of the radii of curvature of the reflecting faces will have to take account of that modification in the path of the light rays.

The means used for compensating the Goldmann lens can also be applied to the Roussel lens, the Coddington equations which are still applicable making it possible to determine the radii of curvature of the lenses.

It will be appreciated that, as in the case of the Goldmann lens, the compensating lens and the Roussel lens may be made of the same material or different materials.

I claim:

1. A contact lens for observation and treatment of the eye by means of a light beam, said contact lens comprising an entrance face by way of which the beam enters, an exit face for application to the cornea of the eye and by way of which the beam issues towards a working point within the eye, and a reflecting face effective by total internal reflection to divert the beam entering at the entrance face towards the exit face, said reflecting face having a curved surface for creating in the contact lens an astigmatism effect which is the reverse of an astigmatism defect of the eye.

2. A contact lens according to claim 1, wherein a principal element is a Goldmann lens and the reflecting face creates the astigmatism defect for an incident light beam which is perpendicular to the entrance face and which impinges on the lens on the side of the reflecting face.

3. A contact lens according to claim 1, wherein a principal element is a Roussel lens and the reflecting face creates the astigmatism defect for an incident light beam which is perpendicular to the entrance face and which impinges on the lens on the side of the reflecting face.

4. A contact lens according to claim 1, wherein the reflecting face is provided by a plano-cylindrical lens.

5. A contact lens according to claim 1, wherein the reflecting face is provided by a plano-toric lens.

6. A contact lens according to claim 1, wherein the entrance face, the exit face and the reflecting face are combined in a single homogenous piece.

7. A contact lens for observation and treatment of the eye by means of a light beam, said contact lens comprising:

a principal element provided with an entrance face by way of which the beam enters, an exit face for application to the cornea of the eye and by way of which the beam issues towards a working point within the eye, and a reflecting face effective by total internal reflection to divert the beam entering at the entrance face towards the exit face; and, means at said reflecting face for providing an astigmatism effect for said beam which is the reverse of an astigmatism defect of the eye.

* * * * *